US011529299B2

(12) United States Patent
Kelly et al.

(10) Patent No.: US 11,529,299 B2
(45) Date of Patent: Dec. 20, 2022

(54) HAIR CARE COMPOSITIONS COMPRISING A 2-PYRIDINOL-N-OXIDE MATERIAL AND AN IRON CHELATOR

(71) Applicant: The Procter & Gamble Company, Cincinnati, OH (US)

(72) Inventors: Casey Patrick Kelly, Wyoming, OH (US); Charles Allen Pettigrew, West Chester, OH (US); Gregory Scot Miracle, Liberty Township, OH (US); Patrick Christopher Stenger, Fairfield, OH (US); Kenneth LaMont Martin, Cincinnati, OH (US); Jennifer Gentry Shields, Cincinnati, OH (US); Justin Angelo Caserta, Mason, OH (US); James Patrick Henry, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 273 days.

(21) Appl. No.: 16/022,994

(22) Filed: Jun. 29, 2018

(65) Prior Publication Data

US 2019/0000735 A1    Jan. 3, 2019

Related U.S. Application Data

(60) Provisional application No. 62/527,116, filed on Jun. 30, 2017.

(51) Int. Cl.
| | | |
|---|---|---|
| *A61Q 5/02* | (2006.01) | |
| *A61Q 5/12* | (2006.01) | |
| *A61K 8/49* | (2006.01) | |
| *A61K 8/44* | (2006.01) | |
| *A61K 8/42* | (2006.01) | |
| *A61K 8/55* | (2006.01) | |
| *A61K 8/41* | (2006.01) | |
| *A61Q 5/00* | (2006.01) | |

(52) U.S. Cl.
CPC .............. *A61K 8/4906* (2013.01); *A61K 8/41* (2013.01); *A61K 8/42* (2013.01); *A61K 8/44* (2013.01); *A61K 8/4926* (2013.01); *A61K 8/55* (2013.01); *A61Q 5/006* (2013.01); *A61Q 5/02* (2013.01); *A61Q 5/12* (2013.01)

(58) Field of Classification Search
None
See application file for complete search history.

(56) References Cited

U.S. PATENT DOCUMENTS

| | | |
|---|---|---|
| 3,792,068 A | 2/1974 | Luedders |
| 3,887,692 A | 6/1975 | Gilman |
| 3,904,741 A | 9/1975 | Jones |
| 4,049,792 A | 9/1977 | Elsnau |
| 4,120,948 A | 10/1978 | Shelton |
| 4,220,548 A * | 9/1980 | Hashimoto ............ A61K 8/463 510/124 |
| 4,359,456 A | 11/1982 | Gosling |
| 4,659,560 A | 4/1987 | Bews et al. |
| 4,711,775 A | 12/1987 | Dittmar et al. |
| 4,906,454 A | 3/1990 | Melanson, Jr. et al. |
| 5,019,375 A | 5/1991 | Tanner |
| 5,298,640 A | 3/1994 | Callaghan |
| 5,429,816 A | 7/1995 | Hofrichter et al. |
| 5,675,013 A | 10/1997 | Hani |
| 5,744,146 A | 4/1998 | Peters et al. |
| 5,762,668 A | 6/1998 | Lee |
| 5,891,424 A | 4/1999 | Bretzler |
| 5,972,319 A | 10/1999 | Linn et al. |
| 5,976,514 A | 11/1999 | Guskey |
| 6,177,066 B1 | 1/2001 | Pataut et al. |
| 6,485,717 B1 | 11/2002 | Scavone et al. |
| 6,503,944 B1 | 1/2003 | Chanchani |
| 6,624,126 B1 | 9/2003 | Kasuga et al. |
| 7,033,576 B2 | 4/2006 | Chevallier et al. |
| 7,033,579 B1 | 4/2006 | Scavone |
| 7,425,321 B2 | 9/2008 | Lemoine et al. |
| 7,531,052 B2 | 5/2009 | Yoshiyama |
| 8,460,720 B2 | 6/2013 | Bergeron et al. |
| 8,574,559 B2 | 11/2013 | Banowski et al. |
| 8,841,247 B2 | 9/2014 | Miracle et al. |
| 8,980,876 B2 | 3/2015 | Schwartz |
| 9,468,596 B2 | 10/2016 | Eizen et al. |
| 9,517,193 B2 | 12/2016 | Fares et al. |
| 9,550,964 B2 | 1/2017 | Miracle |
| 9,586,063 B2 | 3/2017 | Marsh et al. |
| 9,949,920 B2 | 4/2018 | Hakim |

(Continued)

FOREIGN PATENT DOCUMENTS

| | | |
|---|---|---|
| EP | 801947 B1 | 11/1998 |
| EP | 3153151 A1 | 4/2017 |

(Continued)

OTHER PUBLICATIONS

All final and non-final office actions for U.S. Appl. No. 16/021,877 (P&G Case 14861).
All final and non-final office actions for U.S. Appl. No. 16/022,863 (P&G Case AA1238).
Declaration Under 37 CFR 1.132 of Patrick Christopher Stenger dated Dec. 10, 2015 for U.S. Appl. No. 14/463,785 (P&G Case 12161 MC).
Declaration Under 37 CFR 1.132 of Patrick Christopher Stenger dated Mar. 21, 2016 for U.S. Appl. No. 14/463,785 (P&G Case 12161MC).
International Search Report and Written Opinion of the International Searching Authority, PCT/US2018/040284, dated Sep. 19, 2018, 14 pages.

(Continued)

*Primary Examiner* — Jyothsna A Venkat
(74) *Attorney, Agent, or Firm* — Linda M. Sivik

(57) ABSTRACT

The present invention is directed to a hair care composition having an effective amount of a 2-pyridinol-N-oxide material and an effective amount of an iron chelator; wherein the combination of the iron chelator and the 2-pyridinol-N-oxide material provides high anti-fungal efficacy.

4 Claims, No Drawings

(56) References Cited

U.S. PATENT DOCUMENTS

| | | | |
|---|---|---|---|
| 10,543,164 B2 | 1/2020 | Sturgis et al. | |
| 10,555,884 B2 | 2/2020 | Sturgis et al. | |
| 10,905,647 B2 | 2/2021 | Sturgis et al. | |
| 10,966,915 B2 | 4/2021 | Sturgis et al. | |
| 11,045,408 B2 | 6/2021 | Sturgis et al. | |
| 2001/0046479 A1 | 11/2001 | Landa | |
| 2002/0086039 A1 | 7/2002 | Lee et al. | |
| 2003/0235546 A1 | 12/2003 | Mattai et al. | |
| 2004/0247551 A1 | 12/2004 | Yokomaku | |
| 2005/0053572 A1 | 3/2005 | Hwang | |
| 2005/0281767 A1 | 12/2005 | Walling et al. | |
| 2006/0254001 A1 | 11/2006 | Hoeffkes | |
| 2007/0003499 A1 | 1/2007 | Shen | |
| 2007/0203240 A1 | 8/2007 | Oblong et al. | |
| 2010/0130568 A1 | 5/2010 | Mastrodonato | |
| 2011/0076309 A1 | 3/2011 | Hogan et al. | |
| 2011/0076310 A1 | 3/2011 | Fan et al. | |
| 2011/0196786 A1 | 8/2011 | Lacerte et al. | |
| 2013/0045907 A1 | 2/2013 | Lanzalaco | |
| 2013/0045910 A1 | 2/2013 | Miracle | |
| 2013/0059929 A1 | 3/2013 | Koehler | |
| 2013/0109664 A1 | 5/2013 | Schwartz | |
| 2013/0174863 A1 | 7/2013 | Marsh | |
| 2013/0333715 A1* | 12/2013 | Hutton, III | A61K 8/44 132/202 |
| 2014/0139449 A1 | 5/2014 | Tsai | |
| 2014/0154189 A1 | 6/2014 | Polson et al. | |
| 2014/0271517 A1 | 9/2014 | Phinney et al. | |
| 2014/0274852 A1 | 9/2014 | Jiang et al. | |
| 2014/0284852 A1 | 9/2014 | Matusewicz | |
| 2015/0196477 A1 | 7/2015 | Stark | |
| 2016/0074300 A1 | 3/2016 | Salvador | |
| 2016/0235661 A1 | 8/2016 | Changoer et al. | |
| 2016/0310393 A1 | 10/2016 | Chang | |
| 2016/0326091 A1 | 11/2016 | Rudolph | |
| 2016/0354300 A1 | 12/2016 | Thompson | |
| 2017/0088800 A1 | 3/2017 | Miracle | |
| 2017/0172873 A1 | 6/2017 | Banowski | |
| 2017/0252288 A1 | 9/2017 | Lesniak et al. | |
| 2017/0304172 A1 | 10/2017 | Chang | |
| 2018/0311135 A1 | 11/2018 | Chang | |
| 2018/0311136 A1 | 11/2018 | Chang | |
| 2018/0325791 A1 | 11/2018 | Lane | |
| 2019/0000730 A1 | 1/2019 | Abuelhaiga et al. | |
| 2019/0000734 A1 | 1/2019 | Sturgis et al. | |
| 2019/0000747 A1 | 1/2019 | Sturgis et al. | |
| 2019/0276389 A1 | 9/2019 | Wos | |
| 2020/0000694 A9 | 1/2020 | Sturgis | |
| 2020/0078281 A1 | 3/2020 | Wang | |
| 2020/0129415 A1 | 4/2020 | Sturgis et al. | |
| 2020/0214957 A1 | 7/2020 | Sturgis | |
| 2021/0100735 A1 | 4/2021 | Sturgis et al. | |
| 2021/0196617 A1 | 7/2021 | Strugis et al. | |
| 2021/0275423 A1 | 9/2021 | Sturgis et al. | |

FOREIGN PATENT DOCUMENTS

| | | | |
|---|---|---|---|
| GB | 1487812 A | 10/1977 | |
| GB | 2048229 A | 12/1980 | |
| GB | 1347950 A | 3/1985 | |
| JP | H11269042 A | 10/1999 | |
| JP | H11269043 A | 10/1999 | |
| JP | 2003026546 A | 1/2003 | |
| JP | 2006045126 A | 2/2006 | |
| JP | 2007169233 A | 7/2007 | |
| JP | 2008110999 A | 2/2008 | |
| JP | 2011251923 A | 12/2011 | |
| JP | 4950142 B2 | 6/2012 | |
| KR | 20000038214 A | 7/2000 | |
| KR | 20070056207 A | 6/2007 | |
| KR | 20070074690 A | 7/2007 | |
| KR | 100782273 B1 | 12/2007 | |
| KR | 101066797 B1 | 9/2011 | |
| KR | 101114307 B1 | 2/2012 | |
| WO | WO9823258 A1 | 6/1998 | |
| WO | WO2004089092 A1 | 3/2004 | |
| WO | WO2006134160 A2 | 12/2006 | |
| WO | 2012058557 A2 | 5/2012 | |
| WO | 2014139449 A1 | 9/2014 | |
| WO | WO-2017097817 A1 * | 6/2017 | C07C 219/06 |

OTHER PUBLICATIONS

International Search Report and Written Opinion of the International Searching Authority, PCT/US2019/047613, dated Nov. 21, 2019, 15 pages.

International Search Report; International Application No. PCT/US2018/039972; dated Mar. 25, 2019; 10 pages.

PCT International Search Report and Written Opinion for PCT/US2018/040179 dated Sep. 19, 2018.

All Office Actions, U.S. Appl. No. 16/716,540.

Kontoghiorghes, George J.; 2-Hydroxypyridine-N-oxides: effective new chelators in iron mobilisation Biochimica et Biophysica Acta; vol. 924 (1); 1987; pp. 13-18; Elsevier.

Landa et al., "Iron Sequestration on Skin: A New Route to Improved Deodorancy", International Journal Cosmetic Science, vol. 25, 2003, pp. 127-135.

Nivea Fresh Natural Deodorant, pulled from the Internet (www.GNPD.com) 3 pages.

Anonymous: "Tea Tree Natural Deodorant", GNDP, MINTEL, Jun. 1, 2016 (Jun. 1, 2016), XP002768345, the wholedocument, 3 pgs.

Florale Haircare, Stick Out Jam (ID#:2160124), Mintel GNPD [online], [retrieval date: Sep. 21, 2021], the Internet URL: "https://www.gnpd.com/sinatra/recordpage/2160124/'", Aug. 2013.

Orbis, Scalp Ism Conditioner 200 g, Amazon [online], the Internet URL: "https://www.amazon.co.jp/%E3%82%AA%E3%83%AB%E3%83%93%E3%82%B9-ORBIS-%E3%82%B9%E3%82%AB%E3%83%AB%E3%83%97%E3%82%A4%E3%82%BA%E3%83%AO-%E3%82%B3%E3%83%B3%E3%83%87%E3%82%A3%E3%82%B7%E3%83%A7%E3%83%8A%E3%83%BC200g/dp/B019NZFW0A", Jan. 18, 2016 (date of starting dealing in the product), [retrieval date: Sep. 21, 2021, pp. 1-8.

Tokiwa Pharmaceutical Co., Ltd., NOV Shampoo M, Amazon [online], the Internet URL: "https://www.amazon.co.jp/NOV-%E3%83%8E%E3%83%96%E3%82%B7%E3%83%A3%E3%83%B3%E3%83%97%E3%83%BCM/dp/B00E1WQC6O", Jul. 20, 2013 (date of starting dealing in the product), [retrieval date: Sep. 21, 2021], pp. 1-6.

* cited by examiner

HAIR CARE COMPOSITIONS COMPRISING A 2-PYRIDINOL-N-OXIDE MATERIAL AND AN IRON CHELATOR

FIELD OF THE INVENTION

The present invention is directed to hair care compositions comprising a 2-pyridinol-N-oxide material and an effective amount of an iron chelator.

BACKGROUND OF THE INVENTION

1-Hydroxy-4-methyl-6-(2,4,4-trimethylpentyl)-2-pyridone monoethanolamine salt, a 2-pyridinol-N-oxide material, is an anti-dandruff active used in shampoos, conditioners, and other treatments. Surprisingly, iron salt impurities can reduce the efficacy of 2-pyridinol-N-oxide materials. Therefore, there is a need to develop products that mitigate this phenomenon and provide higher efficacy. In the present invention it has been found that select iron chelators and 2-pyridinol-N-oxide materials provide significantly higher levels of anti-fungal activity than 2-pyridinol-N-oxide alone. More importantly and surprisingly and since some iron chelators show anti-fungal activity per se, said combinations of 2-pyridinol-N-oxide and certain iron chelators show anti-fungal activity significantly higher than the sum of anti-fungal activities of the components themselves. By utilizing 2-pyridinol-N-oxide materials in combination with select iron chelators, the present invention delivers compositions and products with superior anti-dandruff performance.

SUMMARY OF THE INVENTION

The present invention is directed to a hair care composition comprising an effective amount of a 2-pyridinol-N-oxide material, an effective amount of an iron chelator; wherein the combination of the iron chelator and the 2-pyridinol-N-oxide material provides high anti-fungal efficacy.

DETAILED DESCRIPTION OF THE INVENTION

While the specification concludes with claims which particularly point out and distinctly claim the invention, it is believed the present invention will be better understood from the following description.

The present invention can comprise, consist of, or consist essentially of the essential elements and limitations of the invention described herein, as well any of the additional or optional ingredients, components, or limitations described herein.

All percentages, parts and ratios are based upon the total weight of the compositions of the present invention, unless otherwise specified. All such weights as they pertain to listed ingredients are based on the active level and, therefore do not include carriers or by-products that may be included in commercially available materials.

The components and/or steps, including those which may optionally be added, of the various embodiments of the present invention, are described in detail below.

All documents cited are, in relevant part, incorporated herein by reference; the citation of any document is not to be construed as an admission that it is prior art with respect to the present invention.

All ratios are weight ratios unless specifically stated otherwise.

All temperatures are in degrees Celsius, unless specifically stated otherwise.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Herein, "effective" means an amount of a subject active high enough to provide a significant positive modification of the condition to be treated. An effective amount of the subject active will vary with the particular condition being treated, the severity of the condition, the duration of the treatment, the nature of concurrent treatment, and like factors.

Herein, "hair care compositions" means products for and/or methods relating to treating hair (human, dog, and/or cat), including, bleaching, coloring, dyeing, conditioning, growing, removing, retarding growth, shampooing, styling; and products and/or methods relating to orally administered materials for enhancing the appearance of hair (human, dog, and/or cat).

The term "2-pyridinol-N-oxide material" encompasses materials that include the unsubstituted 2-pyridinol-N-oxide, substituted 2-pyridinol-N-oxide and their salts and tautomeric structures.

Iron Chelators

In the present invention, iron chelators may have, but not be limited to, the following characteristics:
1. An affinity for iron ions in either the ferrous (iron II) or ferric (III) forms;
2. Materials of Description 1 (above) that have a denticity of four or higher (denticity is the number of groups of a molecule that bind to the iron);
3. Chemical descriptions that are a subset of Description 2:
  a. Either natural or synthetic materials;
  b. Materials of the following chemical classes:
    i. Aminophosphates
    ii Aminocarboxylates
    iii. Hydroxamic acids
    and molecules representing combinations of these chemical classes.

In of the present invention, an iron chelator may be present from the following groups:
(1) Iron chelators represented by the following structure:

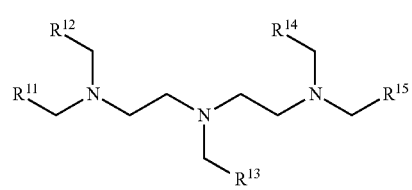

where $R^{11}$, $R^{12}$, $R^{13}$, $R^{14}$, $R^{15}$ are independently selected from the group consisting of $M^1M^2PO_3$, $CO_2M^1$, and mixtures thereof where M¹ and M² is H, a metal salt or ammonium salt, wherein non-limiting examples of the metal salts include Na, K, Ca, Mg, Al salts.

(2) Iron chelators represented by the following structure:

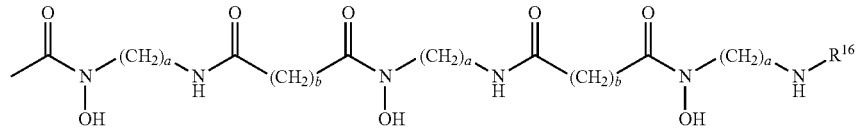

where a is an integer from 2 to 7 wherein any of the CH₂ groups in this unit may be substituted with alkyl or aryl units that may contain heteroatoms (S, N, O, Cl, F, Br or I)

where b is an integer from 1 to 7 wherein any of the CH₂ groups in this unit may be substituted with alkyl or aryl units that may contain heteroatoms (S, N, O, Cl, F, Br or I)

where $R^{16}$ is H or $(CH_2)_n$, where n in an integer from 1 to 6 or is a CH₂ linker unit that may be further substituted at any CH₂ group in the chain with alkyl or aryl units that may contain heteroatoms (S, N, O, Cl, F, Br, or I).

Non-limiting examples of iron chelators include diethylenetriaminepentaacetic acid (DTPA), Diethylenetriaminepentakis (methylenephosphonic acid) (DTPMP), Desferrioxamine, their salts and combinations thereof. The present invention may contain from about 0.01% to about 15% of an iron chelator, alternatively from about 0.3% to about 6%, and alternatively from about 0.5% to about 4%.

2-Pyridinol-N-Oxide Materials

2-Pyridinol-N-oxide materials suitable for use in this invention include a substituted or unsubstituted 2-pyridinol-N-oxide material or a salt thereof. Included within the scope of this invention are tautomers of this material, e.g., 1-hydroxy-2(1H)-pyridinone. The substituted or unsubstituted 2-pyridinol-N-oxide material and its corresponding tautomeric form, 1-hydroxy-2(1H)-pyridinone, are shown below:

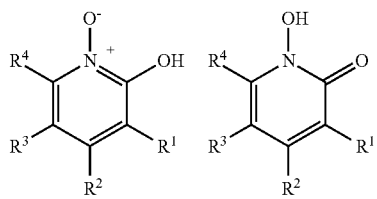

where $R^1$, $R^2$, $R^3$, $R^4$ groups are independently selected from the group consisting of H, Cl, Br, I, F, NO, NO₂, and $(CH_2)_nG$, where each G is independently selected from the group consisting of $(O)_mSO_3M^3$, $(O)_mCO_2M^3$, $(O)_mC(O)(R^5)$, $(O)_mC(O)N(R^5R^6)$, $(O)_mCN$, $(O)_m(R^5)$, and $N(R^5R^6)$, where m is 0 or 1, n is an integer from 0 to 4, $R^5$ and $R^6$ are independently selected from the group consisting of H and a substituted or unsubstituted $C_1$-$C_{12}$ organic group, and $M^3$ is selected from the group consisting of H, a substituted or unsubstituted $C_1$-$C_{12}$ organic group, $+N(R^7R^8R^9R^{10})$, and $1/q\ M'^{q+}$ where M' is selected from the group consisting of an alkali metal of charge q and an alkaline earth metal of charge q, where R7, R8, R9, and R10 are independently selected from the group consisting of H and a substituted or unsubstituted $C_1$-$C_{12}$ organic group, and where any pair of vicinal groups, $R^1$ and $R^2$, $R^2$ and $R^3$, $R^3$ and $R^4$ may be taken together to form another five- or six-membered aromatic or aliphatic ring optionally substituted with one or more groups selected from the group consisting of Cl, Br, I, F, NO, NO₂, CN, $(CH_2)_nG$, and mixtures thereof. Suitable organic groups include $(C_1$-$C_{12})$alkyl, $(C_2$-$C_{12})$alkenyl, and $(C_2$-$C_{12})$alkynyl. The organic group may optionally be substituted and suitable substituent groups include a hydroxyl group, a carboxyl group, and an amino group. 2-pyridinol-N-oxide is also known, for example, as 2-hydroxypyridine-N-oxide, 2-pyridinol-1-oxide, or 2-hydroxypyridine-1-oxide.

In certain aspects, the 2-pyridinol-N-oxide material is a 2-pyridinol-N-oxide material or tautomer thereof according to the formula(s) above, where $R^1$, $R^2$, $R^3$, $R^4$ are independently selected from the group consisting of H, Cl, and $(CH_2)_nG$, where G is independently selected from the group consisting of $(O)_mSO_3M^3$, $(O)_mCO_2M^3$, $(O)_mC(O)(R^5)$, $(O)_mCN$, and $(O)_m(R^5)$, where m is 0 or 1. In other aspects, the 2-pyridinol-N-oxide material is a 2-pyridinol-N-oxide material according to the formula above, where $R^1$, $R^2$, $R^3$, $R^4$ are independently selected from the group consisting of H, $SO_3M^3$, and $CO_2M^3$. In still other aspects, $R^1$, $R^2$, $R^3$, $R^4$ are independently selected from the group consisting of H, $SO_3M^3$, and $CO_2M^3$, where no more than one $R^1$, $R^2$, $R^3$, $R^4$ is $SO_3M^3$ or $CO_2M^3$.

In certain aspects, the 2-pyridinol-N-oxide material is the salt of a substituted or unsubstituted 2-pyridinol-N-oxide material. In these aspects, the hydrogen of the hydroxyl group of the 2-pyridinol-N-oxide material may be substituted with a suitable charge-balancing cation. In these aspects, non-limiting examples of the hydrogen-substituting cation include $Na^+$, $Li^+$, $K^+$, $½Mg^{2+}$, or $½ Ca^{2+}$, substituted ammonium, such as $C_1$-$C_6$ alkanolammnonium, mono-ethanolamine (MEA), tri-ethanolamine (TEA), di-ethanolamine (DEA), or any mixture thereof. In some aspects, the cation may be dissociated from the 2-pyridinol-N-oxide or the 1-hydroxy-2(1H)-pyridinone anion.

In certain aspects, the 2-pyridinol-N-oxide material is of a substituted or unsubstituted 2-pyridinol-N-oxide material. Salts for use herein include those formed from the polyvalent metals barium, bismuth, strontium, copper, zinc, cadmium, zirconium and mixtures thereof.

In some aspects, the 2-pyridinol-N-oxide material is selected from the group consisting of: 6-hydroxy-3-pyridinesulfonic acid, 1-oxide (CAS 191672-18-1); 2-hydroxy-pyridine-1-oxide (CAS 13161-30-3); 2-hydroxy-4-pyridinecarboxylic acid, 1-oxide (CAS 13602-64-7); 5-ethoxy-2-pyridinol, 2-acetate, 1-oxide (CAS 51984-49-7); 1-(3-hydroxy-2-oxido-4-isoquinolinyl)-ethanone (CAS 65417-65-4); 6-hydroxy-3-pyridinecarboxylic acid, 1-oxide (CAS 90037-89-1); 2-methoxy-4-quinolinecarbonitrile, 1-oxide (CAS 379722-76-6); 2-pyridinecarboxylic acid, 6-hydroxy-, 1-oxide (CAS 1094194-45-2); 3-pyridinecarboxylic acid, 2-hydroxy-, 1-oxide (CAS 408538-43-2); 2-pyridinol, 3-nitro-, 1-oxide (CAS 282102-08-3); 3-pyridinepropanenitrile, 2-hydroxy-, 1-oxide (193605-60-6); 3-pyridineethanol, 2-hydroxy-, 3-acetate, 1-oxide (CAS 193605-56-0); 2-pyridinol, 4-bromo-, 1-oxide (CAS 170875-41-9); 2-pyridinol, 4,6-dibromo-, 2-acetate, 1-oxide (CAS 170875-40-8); 2-pyridinol, 4,6-dibromo, 1-oxide (CAS 170875-38-4); 2-pyridinol, 4-(2-aminoethyl)-, 1-oxide (CAS 154403-93-7); 2-pyridinol, 5-(2-aminoethyl)-, 1-oxide (CAS 154403-92-6); 3-pyridinepropanoic acid, α-amino-6-hydroxy-, 1-oxide (CAS 134419-61-7); 2-pyridinol, 3,5-dimethyl, 1-oxide (CAS 102074-62-4); 2-pyridinol, 3-methyl-, 1-oxide (CAS 99969-07-0); 2-pyridinol, 3,5-dinitro, 1-oxide (CAS 98136-47-1); 2-pyridinol, 3,5-dibromo-, 1-oxide (CAS 98136-29-9); 2-pyridinol, 4-methyl-6-(2-methylpropyl)-, 1-oxide (CAS 91408-77-4); 2-pyridinol, 3-bromo-4,6-dimethyl-, 1-oxide (CAS 91408-76-3); 2-pyridinol, 4,5,6-trimethyl-, 1-oxide (CAS 91408-75-2); 2-pyridinol, 6-heptyl-4-methyl-, 1-oxide (CAS 91408-73-0); 2-pyridinol, 6-(cyclohexylmethyl)-4-methyl-, 1-oxide (CAS 91408-72-9); 2-pyridinol, 6-bromo-, 1-oxide (CAS 89284-00-4); 2-pyridinol, 5-bromo-, 1-oxide (CAS 89283-99-8); 2-pyridinol, 3,5-dichloro-4,6-difluoro-, 1-oxide (CAS 33693-37-7); 2-pyridinol, 3,4,5,6-tetrachloro-, 1-oxide (CAS 32835-63-5); 2-pyridinol, 6-methyl-, 1-oxide (CAS 14420-62-3); 2-pyridinol, 5-nitro-, 1-oxide (CAS 14396-03-3); 2-pyridinol, 4-methyl-5-nitro-, 1-oxide (CAS 13602-77-2); 2-pyridinol, 4-chloro-5-nitro-, 1-oxide (CAS 13602-73-8); 2-pyridinol, 4-chloro-, 1-oxide (CAS 13602-65-8); 2-pyridinol, 4-nitro-, 1-oxide (CAS 13602-63-6); and 2-pyridinol, 4-methyl-, 1-oxide (CAS 1952-64-3), and mixtures thereof. These materials are commercially available from, for example, Sigma-Aldrich (St. Louis, Mo.) and/or Aces Pharma (Branford, Conn.).

In certain aspects, the 2-pyridinol-N-oxide material is a 2-pyridinol-N-oxide material selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof.

In certain aspects, the 2-pyridinol-N-oxide material is a 1-Hydroxy-2(1H)-pyridinone material selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2(1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1,2-dihydro-1-hydroxy-2-oxo-4-Pyridinecarboxylic acid, methyl ester (CAS 36979-78-9); 1-hydroxy-5-nitro-2(1H)-Pyridinone (CAS 45939-70-6); and mixtures thereof. These materials are commercially available from, for example, Sigma-Aldrich (St. Louis, Mo.), Princeton Building Blocks (Monmouth Junction, N.J.), 3B Scientific Corporation (Libertyville, Ill.), SynFine Research (Richmond Hill, ON), Ryan Scientific, Inc. (Mt. Pleasant, S.C.), and/or Aces Pharma (Branford, Conn.).

In certain aspects, the 2-pyridinol-N-oxide material is a 2-pyridinol-N-oxide material or tautomer thereof according to the formula(s) below:

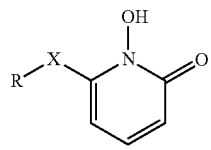

where X is an oxygen or sulfur moiety and R is a substituted or unsubstituted hydrocarbon group having between 1 and 20 carbon atoms. Materials of this class can be synthesized following the procedure disclosed in U.S. Pat. No. 5,675,013.

In certain aspects, the 2-pyridinol-N-oxide material is a 2-pyridinol-N-oxide material or tautomer thereof according to the formula(s) below:

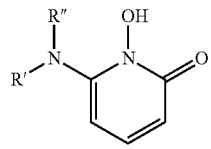

Wherein R' and R" are independently either hydrogen or a substituted or unsubstituted hydrocarbon group having between 1 and 20 carbon atoms. Materials of this class can be synthesized following the procedure disclosed in U.S. Pat. No. 5,675,013. In certain aspects, the 2-pyridinol-N-oxide material is 1-Hydroxy-4-methyl-6-(2,4,4-trimethylpentyl)-2-pyridone monoethanolamine salt.

In the present invention, the hair care composition may contain from about 0.1% to about 10% of a substituted or unsubstituted 2-pyridinol N-oxide material. Alternatively, the hair care composition may contain from about 0.3% to about 3% of a substituted or unsubstituted 2-pyridinol N-oxide material. Alternatively, the hair care composition may contain from about 0.5% to about 2% of a substituted or unsubstituted 2-pyridinol N-oxide material.

Minimum Inhibitory Concentration (MIC)

The minimum inhibitory concentration (MIC) is the inhibitor concentration that causes growth inhibition so that the culture optical density less than or equal to ⅕ (20%) of the culture optical density of the untreated control.

To measure the growth inhibition properties of test materials against *Malassezia*, the following protocol is followed. The *Malassezia furfur* is cultured in 50 ml M. Dixon medium (per one liter: 36 g malt extract (Difco 0186-17), 20 g ox bile (Fluka 70168), 10 ml Tween 40 (Aldrich 27435-6), 6 g peptone (Difco 0118-17), 2 ml oleic acid (Baker 2114-01), and 2 ml glycerol (Sigma G-7893. The pH is adjusted to 5.5 using 1N HCl. The media is autoclaved.

Starting cultures are prepared by incubating freezer stocks with shaking at 33° C. The inoculum of *Malassezia* cells is $5.5 \times 10^5$ cfu/ml. Cells are incubated at 33° C. for two days. After the two day incubation optical density is read and background subtracted. MIC values are determined by averaging the results from two replicate experiments.

TABLE 1

Minimum inhibitory concentrations (MIC) of materials

| Material | MIC (ppm) |
|---|---|
| 1-hydroxy-4-methyl-6-(2,4,4-trimethylpentyl)-2-pyridone monoethanolamine salt | 25 |

TABLE 1-continued

Minimum inhibitory concentrations (MIC) of materials

| Material | MIC (ppm) |
| --- | --- |
| Desferrioxamine | >400 |
| Diethylenetriaminepentaacetic acid (DTPA) | >400 |
| Diethylenetriaminepentakis(methylenephosphonic acid) (DTPMP) | >400 |

Modified Fractional Inhibitory Concentration (MFIC)

A Modified Fractional Inhibitory Concentration (MFIC) is used to determine the combinatorial effects of two chemicals on anti-*Malassezia* activity in a tissue culture setting. MFIC is a measure of the anti-*Malassezia* activity of concentrations of a substituted or unsubstituted 2-pyridinol-N-oxide material that are less than the substituted or unsubstituted 2-pyridinol-N-oxide material's MIC, in combination with other materials.

I. Method Overview:
1. Each MFIC assay is run in duplicate.
2. Low levels of M.Furfur 7892 cells are inoculated into each well of a 96 well plate.
3. Chemical #1 (in our assays this is always a 2-pyridinol-N-oxide material) is added at a concentration equal to ½ the concentration of its MIC concentration.
4. Chemical #2 is titrated (2× concentration reduction) across each well in the same row, starting at 400 ppm.
5. Plates are incubated at 33° C. for 2 days.
6. Optical densities (OD's) are then determined using a spectrophotometer.

II. Data Analysis
1. Inhibition of growth is determined if the culture optical density is less than or equal to ⅕ (20%) of the culture optical density of the untreated control
2. The MFIC is determined as the average value of the lowest concentration value of Material #2 that inhibits growth.

TABLE 2

Modified Fractional Inhibitory concentrations of combinations of materials.

| Material #1 | Material #2 | MFIC (ppm) |
| --- | --- | --- |
| 1-hydroxy-4-methyl-6-(2,4,4-trimethylpentyl)-2-pyridone monoethanolamine salt | Desferrioxamine | 5 |
| 1-hydroxy-4-methyl-6-(2,4,4-trimethylpentyl)-2-pyridone monoethanolamine salt | Diethylenetriaminepentaacetic acid (DTPA) | 37 |
| 1-hydroxy-4-methyl-6-(2,4,4-trimethylpentyl)-2-pyridone monoethanolamine salt | Diethylenetri-aminepentakis(methylenephosphonic acid) (DTPMP) | 50 |
| 1-hydroxy-4-methyl-6-(2,4,4-trimethylpentyl)-2-pyridone monoethanolamine salt | EDTA | 150 |

A lower MFIC value indicates a higher level of efficacy for a combination of materials. The MFIC value of 1-hydroxy-4-methyl-6-(2,4,4-trimethylpentyl)-2-pyridone monoethanolamine salt in combination with EDTA is greater than 100 ppm, indicating this combination has a low level of efficacy.

D. Iron Affinity—Log $K_1$

The strength of the association between a ligand and metal, in this case iron, can be termed iron affinity. A high iron binding affinity is required for chelators to effectively compete with iron salt impurities that reduce the efficacy of 2-pyridinol-N-oxide materials.

Affinity between a metal (M) and ligand (L) can be measured by the stepwise association constant, $K_1$ which describes the following equilibrium:

$$M + L \rightleftharpoons ML; K_1 = \frac{[ML]}{[M][L]}$$

The affinity constant is conveniently expressed as the logarithm (log $K_1$) and the larger the magnitude of this number, the stronger the association between the metal (iron ions in this case) and ligand.

TABLE 3

Iron Binding Affinities of Chelators and their MFIC Values

| Chelator | Log $K_1$ [a] | MFIC (ppm) |
| --- | --- | --- |
| Desferrioxamine | 31 | 5 |
| Diethylenetriaminepentaacetic acid (DTPA) | 28 | 37 |
| Diethylenetriaminepentakis(methylenephosphonic acid) (DTPMP) | 23 | 50 |
| Methylglycine diacetic acid (MGDA) | 16 | >400 |
| Citric Acid | 11 | >400 |

[a] NIST Standard Reference Database 46: Critically Selected Stability Constants of Metal Complexes.

In the present invention, the hair care composition may contain an iron chelator which has a log $K_1$ greater than about 16. Alternatively, the hair care composition may contain an iron chelator which has a log $K_1$ greater than about 20.

The hair care composition of the present invention may be a shampoo, a rinse-off hair conditioner or a leave-on treatment.

Shampoo Composition

The hair care composition of the present invention can be a shampoo. The shampoo composition delivers consumer desired shampooing in addition to scalp anti-dandruff efficacy benefit.

The shampoo composition may comprise from about 0.1 wt % to about 10.0 wt %, alternatively, from about 0.3 wt % to about 3.0 wt %, alternatively from about 0.5% to about 2% of a substituted or unsubstituted 2-pyridinol-N-oxide material in an aqueous carrier. The shampoo composition may also comprise from about 0.01 wt % to about 15.0 wt %, alternatively from about 0.3 wt % to about 6.0 wt %, alternatively from about 0.5% to about 4% of a chelator.

After applying to the hair a shampoo composition as described herein, the shampoo is rinsed from the hair using water.

A. Detersive Surfactant

The shampoo composition may comprise one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. Alternatively, the anionic surfactant is sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium materials, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Alternatively, zwitterionics such as betaines are selected.

Non limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition may also comprise a shampoo gel network, an aqueous carrier, and other additional ingredients described herein.

B. Aqueous Carrier

The shampoo composition comprises a first aqueous carrier. Accordingly, the formulations of the shampoo composition can be in the form of pourable liquids (under ambient conditions). Such compositions will therefore typically comprise a first aqueous carrier, which is present at a level of at least 20 wt %, from about 20 wt % to about 95 wt %, or from about 60 wt % to about 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The first aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

C. Shampoo Gel Matrix

The shampoo composition described herein may comprise a shampoo gel network. The shampoo gel network comprises (i) from about 0.1% to about 20% of one or more fatty alcohols, alternatively, from about 0.5% to about 14%, alternatively, from about 1% to about 10%, alternatively, from about 6% to about 8%, by weight of the shampoo gel network; (ii) from about 0.1% to about 10% of one or more shampoo gel network surfactants, by weight of the shampoo gel network; and (iii) from about 20% to about 95% of an aqueous carrier, alternatively, from about 60% to about 85% by weight of the shampoo gel network.

The fatty alcohols useful herein are those having from about 10 to about 40 carbon atoms, from about 12 to about 22 carbon atoms, from about 16 to about 22 carbon atoms, or about 16 to about 18 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof. Mixtures of cetyl and stearyl alcohol in a ratio of from about 20:80 to about 80:20 are suitable.

The shampoo gel network surfactants may be any of the detersive surfactants described in section "A" herein.

The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful herein includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Conditioner Composition

Hair conditioners are typically applied on hair after rinsing the shampoo composition from the hair. The conditioner composition described herein delivers consumer desired hair conditioning in addition to anti-dandruff benefits.

The conditioner composition comprises from about 0.1 wt % to about 10.0 wt %, alternatively, from about 0.3 wt % to about 3.0 wt %, alternatively, from about 0.5% to about 2% of a 2-pyridinol-N-oxide material in an aqueous carrier. The conditioner composition also comprises from about 0.1 wt % to about 15.0 wt %, alternatively, from about 0.3 wt % to about 3.0 wt %, alternatively, from about 0.5% to about 2% of a chelator. The conditioner composition described herein may also comprise a conditioner gel matrix comprising (1) one or more high melting point fatty materials, (2) a cationic surfactant system, and (3) a second aqueous carrier. After applying to the hair a conditioner composition, the conditioner is rinsed from the hair using water.

A. Cationic Surfactant System

The conditioner gel matrix of the conditioner composition includes a cationic surfactant system. The cationic surfactant system can be one cationic surfactant or a mixture of two or more cationic surfactants. The cationic surfactant system can be selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt.

The cationic surfactant system can be included in the composition at a level by weight of from about 0.1% to about 10%, from about 0.5% to about 8%, from about 0.8% to about 5%, and from about 1.0% to about 4%.

Mono-Long Alkyl Quaternized Ammonium Salt

The monoalkyl quaternized ammonium salt cationic surfactants useful herein are those having one long alkyl chain which has about 22 carbon atoms and alternatively, a C22 alkyl group. The remaining groups attached to nitrogen are independently selected from an alkyl group of from 1 to about 4 carbon atoms; or an aryl group; or an alkoxy, polyoxyalkylene, alkylamido, hydroxyalkyl, or alkylaryl group having up to about 4 carbon atoms.

Mono-long alkyl quaternized ammonium salts useful herein are those having the formula (I):

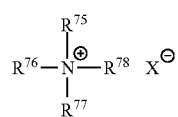

wherein one of $R^{75}$, $R^{76}$, $R^{77}$ and $R^{78}$ is selected from an alkyl group of 22 carbon atoms or an aromatic group; or an aryl group; or an alkoxy, polyoxyalkylene, alkylamido, hydroxyalkyl, or alkylaryl group having up to about 30 carbon atoms; the remainder of $R^{75}$, $R^{76}$, $R^{77}$ and $R^{78}$ are independently selected from an alkyl group of from 1 to about 4 carbon atoms; or an aryl group; or an alkoxy, polyoxyalkylene, alkylamido, hydroxyalkyl, or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of $R^{75}$, $R^{76}$, $R^{77}$ and $R^{78}$ can be selected from an alkyl group of about 22 carbon atoms, the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of about 22 carbons. Exemplary tertiary amido amines include: behenamidopropyldimethylamine, behenamidopropyldiethylamine, behenamidoethyldiethylamine, behenamidoethyldimethylamin. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; alternatively, L-glutamic acid, lactic acid, and/or citric acid. The amines herein can be partially neutralized with any of the acids at a molar ratio of the amine to the acid of from about 1:0.3 to about 1:2, and/or from about 1:0.4 to about 1:1.

Di-Long Alkyl Quaternized Ammonium Salt

Di-long alkyl quaternized ammonium salt can be combined with a mono-long alkyl quaternized ammonium salt or mono-long alkyl amidoamine salt. It is believed that such combination can provide easy-to-rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of from about 10% to about 50%, and/or from about 30% to about 45%.

The di-long alkyl quaternized ammonium salt cationic surfactants useful herein are those having two long alkyl chains having about 22 carbon atoms. The remaining groups attached to nitrogen are independently selected from an alkyl group of from 1 to about 4 carbon atoms; or an aryl group; or an alkoxy, polyoxyalkylene, alkylamido, hydroxyalkyl, or alkylaryl group having up to about 4 carbon atoms.

Di-long alkyl quaternized ammonium salts useful herein are those having the formula (II):

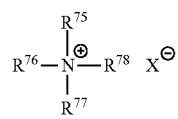

wherein two of $R^{75}$, $R^{76}$, $R^{77}$ and $R^{78}$ is selected from an alkyl group of from 22 carbon atoms; or an aromatic group; or an aryl group; or an alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of $R^{75}$, $R^{76}$, $R^{77}$ and $R^{78}$ can be selected from an alkyl group of from 22 carbon atoms, the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such dialkyl quaternized ammonium salt cationic surfactants include, for example, dialkyl (C22) dimethyl ammonium chloride, ditallow alkyl dimethyl ammonium chloride, dihydrogenated tallow alkyl dimethyl ammonium chloride. Such dialkyl quaternized ammonium salt cationic surfactants also include, for example, asymmetric dialkyl quaternized ammonium salt cationic surfactants.

B. High Melting Point Fatty Compound

The conditioner gel matrix of the conditioner composition includes one or more high melting point fatty compounds. The high melting point fatty compounds useful herein may have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are suitable for use in the conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

High melting point fatty compounds of a single compound of high purity can be used. Single compounds of pure fatty alcohols selected from the group of pure cetyl alcohol, stearyl alcohol, and behenyl alcohol can also be used. By "pure" herein, what is meant is that the compound has a purity of at least about 90%, and/or at least about 95%. These single compounds of high purity provide good rins ability from the hair when the consumer rinses off the composition.

The high melting point fatty compound can be included in the conditioner composition at a level of from about 0.1% to about 20%, alternatively, from about 1% to about 15%, alternatively, from about 1.5% to about 8% by weight of the composition, in view of providing improved conditioning benefits such as slippery feel during the application to wet hair, softness and moisturized feel on dry hair.

C. Aqueous Carrier

The conditioner gel matrix of the conditioner composition includes a second aqueous carrier. Accordingly, the formulations of the conditioner composition can be in the form of pourable liquids (under ambient conditions). Such compositions will therefore typically comprise a second aqueous carrier, which is present at a level of from about 20 wt % to about 95 wt %, or from about 60 wt % to about 85 wt %. The second aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The second aqueous carriers useful in the conditioner composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Leave-On Treatment

The hair care composition of the present invention can be a leave-on treatment. The leave-on treatment composition delivers consumer desired hair conditioning or styling benefit in addition to scalp anti-dandruff efficacy benefit.

The leave-on treatment described herein comprises from about 0.1 wt % to about 10.0 wt %, alternatively, from about 0.3 wt % to about 3.0 wt %, alternatively, from about 0.5% to about 2% of a 2-pyridinol-N-oxide material in an aqueous or a non-aqueous carrier. The leave-on treatment composition also comprises from about 0.1 wt % to about 15.0 wt %, alternatively, from about 0.3 wt % to about 3.0 wt %, alternatively, from about 0.5% to about 2% of the chelator. The leave-on treatment may also comprise (1) one or more rheology modifiers.

The leave-on treatment may comprise an aqueous carrier. Accordingly, the formulations of the leave-on treatment can be in the form of pourable liquids (under ambient conditions). Such compositions will therefore typically comprise an aqueous carrier, which is present at a level of at least 20 wt %, from about 20 wt % to about 95 wt %, or from about 60 wt % to about 85 wt %. The aqueous carrier may comprise water, or a miscible mixture of water and organic solvent, and in one aspect may comprise water with minimal or no significant concentrations of organic solvent, except as otherwise incidentally incorporated into the composition as minor ingredients of other components. The aqueous carriers useful in the leave-on treatment include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Rheology Modifier/Thickener

The hair care compositions mentioned above may also contain one or more rheology modifier/thickener to adjust the rheological characteristics of the composition for better feel, in-use properties and the suspending stability of the composition. For example, the rheological properties are adjusted so that the composition remains uniform during its storage and transportation and it does not drip undesirably onto other areas of the body, clothing or home furnishings during its use. Any suitable rheology modifier can be used. Alternatively, the leave-on treatment may comprise from about 0.01% to about 3% of a rheology modifier, alternatively, from about 0.1% to about 1% of a rheology modifier.

The one or more rheology modifier may be selected from the group consisting of polyacrylamide thickeners, cationically modified polysaccharides, associative thickeners, and mixtures thereof. Associative thickeners include a variety of material classes such as, for example: hydrophobically modified cellulose derivatives; hydrophobically modified alkoxylated urethane polymers, such as PEG-150/decyl alcohol/SMDI copolymer, PEG-150/stearyl alcohol/SMDI copolymer, polyurethane-39; hydrophobically modified, alkali swellable emulsions, such as hydrophobically modified polypolyacrylates, hydrophobically modified polyacrylic acids, and hydrophobically modified polyacrylamides; hydrophobically modified polyethers. These materials may have a hydrophobe that can be selected from cetyl, stearyl, oleayl, and combinations thereof, and a hydrophilic portion of repeating ethylene oxide groups with repeat units from 10-300, alternatively, from 30-200, and alternatively, from 40-150. Examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

Non-limiting examples of additional rheology modifiers include acrylamide/ammonium acrylate copolymer (and) polyisobutene (and) polysorbate 20; acrylamide/sodium acryloyldimethyl taurate copolymer/isohexadecane/polysorbate 80; acrylates copolymer; acrylates/beheneth-25 methacrylate copolymer; acrylates/C10-C30 alkyl acrylate crosspolymer; acrylates/steareth-20 itaconate copolymer; ammonium polyacrylate/Isohexadecane/PEG-40 castor oil; C12-16 alkyl PEG-2 hydroxypropylhydroxyethyl ethylcellulose (HM-EHEC); carbomer; crosslinked polyvinylpyrrolidone (PVP); dibenzylidene sorbitol; hydroxyethyl ethylcellulose (EHEC); hydroxypropyl methylcellulose (HPMC); hydroxypropyl methylcellulose (HPMC); hydroxypropylcellulose (HPC); methylcellulose (MC); methylhydroxyethyl cellulose (MEHEC); PEG-150/decyl alcohol/SMDI copolymer; PEG-150/stearyl alcohol/SMDI copolymer; polyacrylamide/C13-14 isoparaffin/laureth-7; polyacrylate 13/polyisobutene/polysorbate 20; polyacrylate crosspolymer-6; polyamide-3; polyquaternium-37 (and) hydrogenated polydecene (and) trideceth-6; polyurethane-39; sodium acrylate/acryloyldimethyltaurate/dimethylacrylamide; crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E 10M, Benecel K35M, Optasense RMC70, ACULYN™33, ACULYN™46, ACULYN™22, ACULYN™44, Carbopol Ultrez 20, Carbopol Ultrez 21, Carbopol Ultrez 10, Carbopol 1342, Sepigel™ 305, Simulgel™600, Sepimax Zen, and/or combinations thereof. A non exclusive list of suitable thickeners for use herein include xanthan, guar, hydroxypropyl guar, scleroglucan, methyl cellulose, ethyl cellulose (commercially available as Aquacote (Registered trademark), hydroxyethyl cellulose (Natrosol (Registered trademark), carboxymethyl cellulose, hydroxypropylmethyl cellulose, microcrystalline cellulose, hydroxybutylmethyl cellulose, hydroxypropyl cellulose (Klucel (Registered trademark), hydroxyethyl ethyl cellulose, cetyl hydroxyethyl cellulose (Natrosol (Registered trademark Plus 330), N-vinylpyrollidone (Povidone (Registered trademark), Acrylates/Ceteth-20 Itaconate Copolymer (Structure (Registered trademark 3001), hydroxypropyl starch phosphate (Structure (Registered trademark ZEA), polyethoxylated urethanes or polycarbamyl polyglycol ester (e.g. PEG-150/Decyl/SMDI copolymer=Aculyn (Registered trademark 44, PEG-150/Stearyl/SMDI copolymer=Aculyn 46 (Registered trademark), trihydroxystearin (Thixcin (Registered trademark) acrylates copolymer (e.g. Aculyn (Registered trademark 33) or hydrophobically modified acrylate copolymers (e.g. Acrylates/Steareth-20 Methacrylate Copolymer=Aculyn (Registered trademark 22), and fatty alcohols, such as cetyl and stearyl alcohol, and combinations thereof.

pH

The hair care compositions mentioned above may also comprise one or more pH adjusting material. The compositions may have a pH in the range from about 2 to about 10, at 25° C. Alternatively, the shampoo composition, rinse-off conditioner composition, and/or leave-on treatment may have a pH in the range of from about 2 to about alternatively, from about 3.5 to about 5, alternatively, from about 5.25 to about 7.

The hair care compositions mentioned above may further comprise one or more pH buffering agent. Suitable buffering agents are well known in the art and include for example ammonia/ammonium acetate mixture and monoethanolamine (MEA). Alternatively, the shampoo composition and/or rinse-off conditioner composition may comprise citric acid, wherein the citric acid acts as a buffer.

Additional Components

The shampoo composition, conditioner compositions, and/or leave-on treatments described herein may optionally comprise one or more additional components known for use in hair care or personal care products, provided that the additional components are physically and chemically compatible with the essential components described herein, or do not otherwise unduly impair product stability, aesthetics or performance. Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care compositions include conditioning agents, natural cationic deposition polymers, synthetic cationic deposition polymers, other anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

1. Conditioning Agent

The hair care compositions may comprise one or more conditioning agents. Conditioning agents include materials that are used to give a particular conditioning benefit to hair. The conditioning agents useful in the hair care compositions of the present invention typically comprise a water-insoluble, water-dispersible, non-volatile, liquid that forms emulsified, liquid particles. Suitable conditioning agents for use in the hair care composition are those conditioning agents characterized generally as silicones, organic conditioning oils or combinations thereof, or those conditioning agents which otherwise form liquid, dispersed particles in the aqueous surfactant matrix.

One or more conditioning agents are present from about 0.01 wt % to about 10 wt %, from about 0.1 wt % to about 8 wt %, and from about 0.2 wt % to about 4 wt %, by weight of the composition.

Silicone Conditioning Agent

The compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, epoxy groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the polymer can be in an emulsified form with droplet size of about 10 nm to about 30 micrometers Organic Conditioning Materials The conditioning agent of the compositions of the present invention may also comprise at least one organic conditioning material such as oil or wax, either alone or in combination with other conditioning agents, such as the silicones described above. The organic material can be nonpolymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-20 200, PEG-400, PEG-600, PEG-1000, PEG-2M, PEG-7M, PEG-14M, PEG-45M and mixtures thereof.

Benefit Agents

The hair care composition may further comprise one or more additional benefit agents. The benefit agents comprise a material selected from the group consisting of anti-dandruff agents, anti-fungal agents, anti-itch agents, anti-bacterial agents, anti-microbial agents, moisturization agents, anti-oxidants, vitamins, lipid soluble vitamins, perfumes, brighteners, enzymes, sensates, attractants, dyes, pigments, bleaches, and mixtures thereof.

The hair care composition may further comprise one or more additional anti-dandruff active agents may be present in the hair care composition and may include climbazole, ketoconazole, itraconazole, econazole, elubiol and combinations thereof.

The hair care compositions of the present invention may be presented in typical hair care formulations. They may be in the form of solutions, dispersion, emulsions, powders, talcs, encapsulated, spheres, spongers, solid dosage forms, foams, and other delivery mechanisms. The compositions of the present invention may be hair tonics, leave-on hair products such as treatment, and styling products, rinse-off hair products such as shampoos, and treatment products; and any other form that may be applied to hair.

The hair care compositions may be provided in the form of a porous, dissolvable solid structure, such as those disclosed in U.S. Patent Application Publication Nos. 2009/0232873; and 2010/0179083, which are incorporated herein by reference in their entirety. Accordingly, the hair care compositions comprise a chelator, a buffer system comprising an organic acid, from about 23% to about 75% surfactant; from about 10% to about 50% water soluble polymer; and optionally, from about 1% to about 15% plasticizer; such that the hair care composition is in the form of a flexible porous dissolvable solid structure, wherein said structure has a Percent open cell content of from about 80% to about 100%.

The hair care compositions may be in the form of a porous dissolvable solid structure comprising a chelator; a buffer system comprising an organic acid from about 23% to about 75% surfactant; wherein said surfactant has an average ethoxylate/alkyl ratio of from about 0.001 to about 0.45; from about 10% to about 50% water soluble polymer; and from about 1% to about 15% plasticizer; and wherein said article has a density of from about 0.03 $g/cm^3$ to about 0.20 $g/cm^3$.

The hair care compositions may be in the form of a viscous liquid comprising a chelator; a buffer system comprising an organic acid from 5-20% surfactant and a polycarboxylate rheology modifier; wherein the polycarboxylate is specifically chosen to be effective at the high electrolyte levels resulting from the incorporation of the key buffer system and chelator used for this invention. Non-limiting examples include acrylates/C10-C30 alkyl acrylate crosspolymers such as Carbopol EDT2020, 1342, 1382, etc. from Lubrizol. Rheology benefits of these actives in our embodiments include stability, ease of dispensing, smoothness of spreading, etc.

The hair care compositions are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

EXAMPLES

The following examples illustrate embodiments of the invention described herein. The exemplified oxidative dyeing, rinse-off conditioner, and shampoo compositions can be prepared by conventional formulation and mixing techniques. It will be appreciated that other modifications of the oxidative dyeing compositions, rinse-off conditioner compositions, and shampoo compositions within the skill of those in the formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

Shampoo Composition Examples

| Ingredients | Shampoo Example 1 wt % | Shampoo Example 2 wt % | Shampoo Example 3 wt % |
|---|---|---|---|
| Water Purified | Q.S to 100 | Q.S to 100 | Q.S to 100 |
| Sodium Laureth 3 Sulfate | 6.1 | 6.1 | 6.1 |
| Sodium Lauryl Sulfate | 10.0 | 10.0 | 10.0 |
| Laureth-4 | 0.9 | 0.9 | 0.9 |
| Dimethicone 330M cps | 0.5 | 0.5 | 0.5 |
| Glycol Distearate | 1.5 | 1.5 | 1.5 |
| Polyquaternium-6 | 0.32 | 0.32 | 0.32 |
| Sodium Benzoate | 0.27 | 0.52 | 0.52 |
| Citric acid 50% Solution | 0.52 | 0.035 | 0.035 |
| Methylchloroisothiazolinone/methylisothiazolinone | 0.035 | 1.66 | 1.66 |
| Sodium chloride | 1.66 | 0.65 | 0.65 |
| Fragrance | 0.65 | 0.05 | 0.05 |
| DL-Panthenol | 0.03 | 0.03 | 0.03 |
| Panthenyl Ethyl ether | 0.03 | 1 | 1 |
| 1-Hydroxy-4-methyl-6-(2,4,4-trimethylpentyl)-2-pyridone monoethanolamine salt[1] | 1 | 1 | 1 |
| Diethylenetriaminepentakis(methylenephosphonic acid) (DTPMP) | 1 | | |
| Diethylenetriaminepentaacetic acid (DTPA) | | 1 | |
| Desferrioxamine | | | 1 |

| Ingredients | Shampoo Example 4 wt % | Shampoo Example 5 wt % | Shampoo Example 6 wt % | Shampoo Example 7 wt % |
|---|---|---|---|---|
| Water Purified | Q.S to 100 | Q.S to 100 | Q.S to 100 | Q.S to 100 |
| Sodium Laureth 3 Sulfate | 6.1 | 6.1 | 6.1 | 6.1 |
| Sodium Lauryl Sulfate | 10.0 | 10.0 | 10.0 | 10.0 |
| Laureth-4 | 0.9 | 0.9 | 0.9 | 0.9 |
| Dimethicone 330M cps | 0.5 | 0.5 | 0.5 | 0.5 |
| Glycol Distearate | 1.5 | 1.5 | 1.5 | 1.5 |
| Polyquaternium-6 | 0.32 | 0.32 | 0.32 | 0.32 |
| Sodium Benzoate | 0.27 | 0.27 | 0.27 | 0.27 |
| Citric acid 50% Solution | 0.52 | 0.52 | 0.52 | 0.52 |
| Methylchloroisothiazolinone/methylisothiazolinone | 0.035 | 0.035 | 0.035 | 0.035 |
| Sodium chloride | 1.66 | 1.66 | 1.66 | 1.66 |
| Fragrance | 0.65 | 0.65 | 0.65 | 0.65 |
| DL-Panthenol | 0.03 | 0.03 | 0.03 | 0.03 |
| Panthenyl Ethyl ether | 0.03 | 0.03 | 0.03 | 0.03 |
| 1-Hydroxy-4-methyl-6-(2,4,4-trimethylpentyl)-2-pyridone monoethanolamine salt[1] | 0.5 | 0.75 | 0.1 | 10 |
| Diethylenetriaminepentakis(methylenephosphonic acid) (DTPMP) | 5 | 5 | 15 | 0.1 |

Additional Shampoo Examples

| Ingredient | Shampoo Example 8 | Shampoo Example 9 | Shampoo Example 10 |
|---|---|---|---|
| Sodium lauryl ether sulfate (SLE3S) | | 6 | 6 |
| Sodium cocoyl isethionate | | | |
| Sodium lauryl sulfate (SLS) | 1.5 | 7 | 7 |
| Sodium lauryl ether sulfate (SLE1S) | 10.5 | | |
| Disodium laureth sulfosuccinate | | | |
| Sodium lauryl sulfoacetate | | | |
| Sodium Lauroyl Sarcosinate | | | |
| Cocoamidopropyl Hydroxysultaine | | | |
| Cocoamidopropyl Betaine | 1 | 2 | 2 |
| Coconut monoethanol amide (CMEA) | | 0.85 | 0.85 |
| Dimethicone | 1 | 1 | 1 |
| Ethylene glycol distearate (EGDS) | 1.5 | 1.5 | 1.5 |
| Jaguar ® C500[1] | 0.25 | 0.25 | |
| Synthetic Cationic Polymer AMT[2] | | | 0.1 |
| Polydiallyldimethylammonium chloride (DADMAC) | | | |
| Excel Guar[3] | | | |
| 1-Hydroxy-4-methyl-6-(2,4,4-trimethylpentyl)-2-pyridone monoethanolamine salt[1] | 1 | 1 | 1 |

| Ingredient | Shampoo Example 11 | Shampoo Example 12 | Shampoo Example 13 |
|---|---|---|---|
| Diethylenetriaminepentakis(methylenephosphonic acid) (DTPMP) | 1 | 1 | 1 |
| pH | 6 | 6 | 6 |
| Water-USP Purified & Minors | Q.S. to 100 | Q.S. to 100 | Q.S. to 100 |

| Ingredient | Shampoo Example 11 | Shampoo Example 12 | Shampoo Example 13 |
|---|---|---|---|
| Sodium lauryl ether sulfate (SLE3S) | 6 | 9 | |
| Sodium cocoyl isethionate | | | 8.5 |
| Sodium lauryl sulfate (SLS) | 7 | 6 | |
| Sodium lauryl ether sulfate (SLE1S) | | | |
| Disodium laureth sulfosuccinate | | | 8.5 |
| Sodium lauryl sulfoacetate | | | 2.5 |
| Sodium Lauroyl Sarcosinate | | | 0.75 |
| Cocoamidopropyl Hydroxysultaine | | | 1.5 |
| Cocoamidopropyl Betaine | 2 | 2 | 2 |
| Coconut monoethanol amide (CMEA) | | | |
| Dimethicone | 1 | | |
| Ethylene glycol distearate (EGDS) | 1.5 | | |
| Jaguar ® C500[2] | | | |
| Synthetic Cationic Polymer AMT[3] | | | 0.15 |
| Polydiallyldimethylammonium chloride (DADMAC) | 0.1 | | 1 |
| Excel Guar[4] | | 0.1 | 1 |
| 1-Hydroxy-4-methyl-6-(2,4,4-trimethylpentyl)-2-pyridone monoethanolamine salt[1] | 1 | 1 | 1 |
| Diethylenetriaminepentakis(methylenephosphonic acid) (DTPMP) | 1 | 1 | 1 |
| pH | 6 | 6 | 6 |
| Water-USP Purified & Minors | Q.S. to 100 | Q.S. to 100 | Q.S. to 100 |

[1]Synonym of the material is piroctone olamine, available from Combi-Blocks, Inc.
[2]Cationic polymer derived from a natural gum with low aqueous viscosity
[3]Cationic synthetic copolymer
[4]Cationic plant derived polymer Examples of Shampoo Compositions Containing Gel Network Shampoo Gel Network Method of Preparation The shampoo gel network may be formed by combining fatty alcohols and surfactants in the ratio of 1:1 to 40:1, alternatively, from 2:1 to 20:1, alternatively, from 3:1 to 10:1. The formation of a shampoo gel network involves heating a dispersion of the fatty alcohol in water with the surfactant to a temperature above the melting point of the fatty alcohol. During the mixing process, the fatty alcohol melts, allowing the surfactant to partition into the fatty alcohol droplets. The surfactant brings water along with it into the fatty alcohol. This changes the isotropic fatty alcohol drops into liquid crystalline phase drops. When the mixture is cooled below the chain melt temperature, the liquid crystal phase is converted into a solid crystalline gel network.

| Ingredient | Shampoo Ex. 14 | Shampoo Ex. 15 | Shampoo Ex. 16 |
|---|---|---|---|
| Water-USP Purified & Minors | Q.S. to 100 | Q.S. to 100 | Q.S. to 100 |
| Sodium Laureth Sulfate (SLE1S) | 12 | 12 | 14 |
| Sodium Lauryl Sulfate (SLS) | 1.5 | 1.5 | |
| Cocoamidoproply Betaine (CapB) | 1.7 | 1.7 | 1.7 |
| Gel Network | 1 | 2 | 2 |
| Guar Hydroxypropyltrimonium Chloride | 0.3 | 0.3 | 0.3 |
| Polyquaternium 6 (DADMAC) | 0.1 | 0.1 | 0.1 |
| Ethylene Glycol Distearate | 1.5 | 1.5 | |
| Trihydroxy Stearin (Thixcin) | | | 0.1 |
| Dimethicone/Dimethiconol | 1 | 0.5 | 0.5 |
| Citric Acid | 1 | 1 | 1 |
| Sodium Citrate Dihydrate | 1 | 1 | 1 |
| Acrylates/C10-C30 alkyl acrylate crosspolymers | | | |
| Kathon | 0.0005 | 0.0005 | 0.0005 |
| Sodium Benzoate | 0.25 | 0.25 | 0.25 |
| 1-Hydroxy-4-methyl-6-(2,4,4-trimethylpentyl)-2-pyridone monoethanolamine salt[1] | 1 | 1 | 1 |
| Diethylenetriaminepentaacetic acid (DTPA) | 1 | 1 | 1 |
| Perfume | 0.8 | 0.8 | 0.8 |
| Sodium Chloride[2] | 0-3 | 0-3 | 0-3 |
| Sodium Xylene Sulfonate[2] | 0-3 | 0-3 | 0-3 |

[1]Synonym of the material is piroctone olamine, available from Combi-Blocks, Inc.
[2]Level adjusted to reach desired viscosity Examples of Rinse-Off Conditioner Compositions

| Ingredients | Rinse-off Conditioner Ex 1 Wt % | Rinse-off Conditioner Ex 2 Wt % |
|---|---|---|
| Amodimethicone 10000 cps | 0.5 | 0.5 |
| Citric acid anhydrous | 0.13 | 0.13 |
| DL-Panthenol 56% solution | 0.054 | 0.054 |
| Panthenyl Ethyl ether | 0.03 | 0.03 |
| Perfume | 0.5 | 0.5 |

| Ingredients | | |
|---|---|---|
| Hydroxypropyl guar (Jaguar HP-105) | 0.35 | 0.35 |
| Quaternium-18 | 0.75 | 0.75 |
| Steramidopropyldimethylamine | 1 | 1 |
| Gryceryl stearate | 0.25 | 0.25 |
| Cetearyl alcohol and Polysorbate 60 Emulsion[1] | 0.5 | 0.5 |
| Cetyl alcohol | 1.2 | 1.2 |
| Stearyl alcohol | 0.8 | 0.8 |
| Benzyl alcohol | 0.4 | 0.4 |
| Methylchloroisothiazolinone/methylisothiazolinone | 0.033 | 0.033 |
| 1-Hydroxy-4-methyl-6-(2,4,4-trimethylpentyl)-2-pyridone monoethanolamine salt[1] | 1 | 1 |
| Diethylenetriaminepentaacetic acid (DTPA) | 1 | |
| Desferrioxamine | | 1 |
| Water Purified | QS to 100 | QS to 100 |

| Ingredients | Rinse-off Conditioner Ex. 3 | Rinse-off Conditioner Ex. 4 |
|---|---|---|
| Water-USP Purified & Minors | QS to 100% | QS to 100% |
| BTMS[2] | 3.76 | 3.76 |
| Cetyl alcohol | 1.3 | 1.3 |
| Stearyl alcohol | 3.2 | 3.2 |
| Soy Oligomer[3] | 1.0 | — |
| Aminosilicone[4] | — | 1.0 |
| 1-Hydroxy-4-methyl-6-(2,4,4-trimethylpentyl)-2-pyridone monoethanolamine salt[1] | 1 | 1 |
| Diethylenetriaminepentakis (methylenephosphonic acid) (DTPMP) | 1 | 1 |
| Perfume | 0.5 | 0.5 |
| Benzyl Alcohol | 0.4 | 0.4 |
| Preservatives | 0.03 | 0.03 |

| Ingredients | Rinse-off Conditioner Ex. 5 | Rinse-off Conditioner Ex. 6 |
|---|---|---|
| Water-USP Purified & Minors | QS to 100% | QS to 100% |
| BTMS[2] | 3.76 | 3.76 |
| Cetyl alcohol | 1.3 | 1.3 |
| Stearyl alcohol | 3.2 | 3.2 |
| Soy Oligomer[3] | — | — |
| Aminosilicone[4] | 1 | 1 |
| 1-Hydroxy-4-methyl-6-(2,4,4-trimethylpentyl)-2-pyridone monoethanolamine salt[1] | 1 | 1 |
| Diethylenetriaminepentaacetic acid (DTPA) | 1 | |
| Desferrioxamine | | 1 |
| Perfume | 0.5 | 0.5 |
| Benzyl Alcohol | 0.4 | 0.4 |
| Preservatives | 0.03 | 0.03 |

[1]Synonym of the material is piroctone olamine, available from Combi-Blocks, Inc.
[2]Behenyltrimethylammonium methylsulfate from Feixiang.
[3]HY-3050 from Dow Corning.
[4]Y-14945; 10,000 cP aminodimethicone from Momentive

Examples of Leave-On Treatment Compositions

| Ingredients | LOT Ex. 1 | LOT Ex. 2 |
|---|---|---|
| Dipropyleneglycol Monomethylether | 0.5 | 0.5 |
| Disodium Ethylene diamine diacetic acid | 0.141 | 0.141 |
| PEG-40 Hydrogenated Castor Oil | 0.5 | 0.5 |
| Polysorbate 80[2] | 0.12 | 0.12 |
| Amodimethicone and Cetrimonium Chloride | 1.81 | 1.81 |
| Polyquaternium 11[3] | 1.335 | 1.335 |
| Citric Acid Anhydrous | 0.08 | 0.08 |
| 2-Amino-2-methyl-1-propanol | 0.1 | 0.1 |
| DMDM Hydantoin (55%)[4] | 0.37 | — |
| Benzyl Alcohol | — | 0.4 |
| Neolone 950 Preservative[5] | — | 0.053 |
| Perfume | 0.2 | 0.2 |
| 1-Hydroxy-4-methyl-6-(2,4,4-trimethylpentyl)-2-pyridone monoethanolamine salt[1] | 1 | 1 |
| Diethylenetriaminepentaacetic acid (DTPA) | 1 | |
| Desferrioxamine | | 1 |
| Water-USP Purified & Minors | QS to 100% | QS to 100% |

[1]Synonym of the material is piroctone olamine, available from Combi-Blocks, Inc.
[2]Nonionic surfactant and emulsifier derived frompolyethoxylated sorbitan and oleic acid
[3]Copolymer of vinylpyrrolidone and quaternized dimethylaminoethyl methacrylate
[4]1,3-Bis(hydroxymethyl)-5,5-dimethylimidazolidine-2,4-dione
[5]Preservative containing Methylisothiazolinone

Additional Examples/Combinations

A. A hair care composition comprising:

a) from about 0.1% to about 10% of a substituted or unsubstituted 2-pyridinol-N-oxide material;

b) from about 0.01% to about 15% of an iron chelator wherein the combination of the iron chelator and the substituted or unsubstituted 2-pyridinol-N-oxide material has a modified fractional inhibitor concentration of less than or equal to about 100 ppm and is selected from the group consisting of:

i. Iron chelators represented by the following structure:

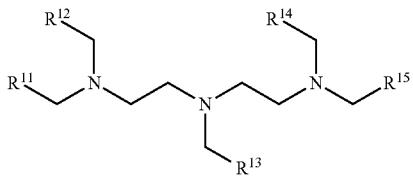

where $R^{10}$, $R^{11}$, $R^{12}$, $R^{13}$, $R^{14}$ are selected from the group consisting of $M^1M^2PO_3$, $CO_2M^1$, and mixtures thereof where $M^1$ and $M^2$ are independently selected from the group consisting of H, ammonium, and a metal salt, wherein the metal salt is selected from the group consisting of sodium, potassium, calcium, magnesium, and aluminum;

ii. Iron chelators represented by the following structure:

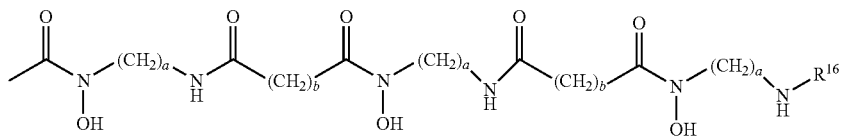

where a is an integer from 2 to 7 wherein any of the $CH_2$ groups in this unit may be substituted with alkyl or aryl units that may contain heteroatoms (S, N, O, Cl, F, Br or I)

where b is an integer from 1 to 7 wherein any of the $CH_2$ groups in this unit may be substituted with alkyl or aryl units that may contain heteroatoms (S, N, O, Cl, F, Br or I)

where $R^{16}$ is H or $(CH_2)_n$, where n in an integer from 1 to 6 or is a $CH_2$ linker unit that may be further substituted at any $CH_2$ group in the chain with alkyl or aryl units that may contain heteroatoms (S, N, O, Cl, F, Br, or I);

and mixtures of i and ii thereof;

c) from about 40% to about 95% aqueous carrier.

B, The hair care composition according to Paragraph A, wherein the iron chelator has a log $K_1$ greater than about 16.

C. The hair care composition according to Paragraph A-B, wherein the iron chelator has a log $K_1$ greater than about 20.

D. The hair care composition according to Paragraph A-C, where the substituted or unsubstituted 2-pyridinol-N-oxide material comprises the molecular structure:

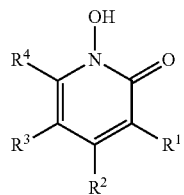

wherein $R^1$, $R^2$, $R^3$, $R^4$ are independently selected from the group consisting of H, Cl, Br, I, F, NO, $NO_2$, $(CH_2)_nG$, and mixtures thereof, wherein each G is independently selected from the group consisting of $(O)_mSO_3M^3$, $(O)_mCO_2M^3$, $(O)_mC(O)(R^5)$, $(O)_mC(O)N(R^5R^6)$, $(O)_mCN$, $(O)_m(R^5)$, $N(R^5R^6)$, and mixtures thereof, wherein m is 0 or 1, and wherein n is an integer from 0 to 4, and wherein $R^5$ and $R^6$ are independently selected from the group consisting of H and a substituted or unsubstituted C1-C12 organic group, and wherein $M^3$ is selected from the group consisting of H, a substituted or unsubstituted $C_1$-$C_{12}$ organic group, $+N(R^7R^8R^9R^{10})$, and 1/q M'q+ wherein M' is selected from the group consisting of an alkali metal of charge q and an alkaline earth metal of charge q, where R7, R8, R9, and R10 are independently selected from the group consisting of H and a substituted or unsubstituted C1-C12 organic group, and wherein any pair of vicinal groups, $R^1$ and $R^2$, $R^2$ and $R^3$, $R^3$ and $R^4$, may be taken together to form another five- or six-membered aromatic or aliphatic ring optionally substituted with one or more groups selected from the group consisting of Cl, Br, I, F, NO, $NO_2$, CN, $(CH_2)_nG$, and mixtures thereof.

E. The hair care composition according to Paragraph A-D, wherein $R^1$, $R^2$, $R^3$, $R^4$ are selected from the group consisting of H, Cl, and $(CH_2)_nG$, wherein G is selected from the group consisting of $(O)_mSO_3M^3$, $(O)_mCO_2M^3$, $(O)_mC(O)(R^5)$, $(O)_mCN$, and $(O)_m(R^5)$, wherein m is 0 or 1.

F. The hair care composition according to Paragraph A-E, wherein said substituted or unsubstituted 2-pyridinol-N-oxide material is 1-hydroxy-4-methyl-6-(2,4,4-trimethylpentyl)-2-pyridone monoethanolamine salt.

G. The hair care composition according to Paragraph A-F, wherein the iron chelator is selected from the group consisting of diethylenetriaminepentaacetic acid (DTPA), Diethylenetriaminepentakis (methylenephosphonic acid) (DTPMP), Desferrioxamine and mixtures thereof.

H. The hair care composition according to Paragraph A-G, wherein the iron chelator is diethylenetriaminepentaacetic acid (DTPA).

I. The hair care composition according to Paragraph A-H, wherein the iron chelator is Diethylenetriaminepentakis (methylenephosphonic acid) (DTPMP).

J. The hair care composition according to Paragraph A-I, wherein the iron chelator is Desferrioxamine K. The hair care composition according to Paragraph A-J, wherein the substituted or unsubstituted 2-pyridinol N-oxide material is from about 0.3% to about 3%.

L. The hair care composition according to Paragraph A-K, the substituted or unsubstituted 2-pyridinol N-oxide material is from about 0.5% to about 2%.

M. The hair care composition according to Paragraph A-L, wherein the iron chelator is from about 0.3% to about 6%.

N. The hair care composition according to Paragraph A-M, wherein the iron chelator is from about 0.5% to about 4%.

O. The hair care composition according to Paragraph A-N, wherein the modified fractional inhibitor concentration of less than or equal to about 70 ppm.

P. The hair care composition according to Paragraph A-O, wherein the modified fractional inhibitor concentration of less than or equal to about 60 ppm.

Q. The hair care composition according to Paragraph A-P, wherein the modified fractional inhibitor concentration of less than or equal to about 50 ppm.

R. The hair care composition according to Paragraph A-Q, wherein the hair composition is a shampoo composition further comprising:

a. from about 5% to about 45% of one or more detersive surfactants, by weight of the shampoo composition; and b. from about 75% to about 95% of an aqueous carrier, by weight of the shampoo composition.

S. The hair care composition according to Paragraph A-R, wherein the hair composition is a rinse-off hair conditioner composition further comprising a) from about 50% to about 80% of an aqueous carrier, by weight of the conditioner composition and b) a conditioner gel matrix comprising: (i) from 0.1% to about 20% of one or more high melting point fatty compound, by weight of the conditioner gel matrix; (ii) from about 0.1% to about 10% of a cationic surfactant system, by weight of the conditioner gel matrix; and (iii) at least 20% of a second aqueous carrier, by weight of the conditioner gel matrix.

T. The hair care composition according to Paragraph A-S, wherein the hair composition is a leave-on treatment composition further comprising: (i) from 0.1% to about 20% of one or more high melting point fatty compound, by weight of the conditioner gel matrix; (ii) from about 0.1% to about 10% of a cationic surfactant system, by weight of the conditioner gel matrix; and (iii) at least 20% of a second aqueous carrier, by weight of the conditioner gel matrix.

U. The hair care composition according to Paragraph A-T, wherein the hair composition is a leave-on treatment composition further comprising 0.01-4% of a rheology modifier.

V. The hair care composition according to Paragraph A-U, wherein the rheology modifier is a polymeric rheology modifier (or Polyacrylamide & C13-14 Isoparaflin & Laureth-7.

W. The hair care composition according to Paragraph A-V, wherein the hair composition further comprises one or more additional anti-dandruff active agents selected from the group consisting of climbazole, ketoconazole, itraconazole, econazole, elubiol and combinations thereof.

X. Use of the hair care composition according to Paragraph A-X, for treating hair.

Y. Use according to Paragraph X, for treating cosmetically hair against dandruff (without cosmetic, I am afraid that we fall into a medical use).

Y1. Use according to Paragraph X, for improving the cosmetic aspect of hair and the scalp against dandruff (without cosmetic, I am afraid that we fall into a medical use).

Z. Use according to Paragraph X, for inhibiting the growth of *Malassezia*.

Z1. Use according to Paragraph X for providing an anti-fungal activity onto hair.

A1. Use according to Paragraph X for mitigating anti-dandruff onto hair.

A2. Use according to Paragraph X, wherein the hair composition comprises from 0.1% to 10% of 11-hydroxy-4-methyl-6-(2,4,4-trimethylpentyl)-2-pyridone monoethanolamine salt and from 0.01% to a 15% of an iron chelator which is selected from the group consisting of diethylenetriaminepentaacetic acid (DTPA), Diethylenetriaminepentakis (methylenephosphonic acid) (DTPMP), Desferrioxamine, and mixtures thereof.

A3. The hair care composition according to Paragraph A-W for use as an antifungal agent.

A4. The hair care composition according to Paragraph A3, for use as an antifungal agent against *Malassezia*.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A shampoo composition comprising:
a) from about 10% to about 20% of a detersive surfactant
b) from about 0.3% to about 3% of 1-hydroxy-4-methyl-6-(2,4,4-trimethylpentyl)-2-pyridone monoethanolamine salt;
c) from about 0.3% to about 6% of Diethylenetriaminepentakis (methylenephosphonic acid) wherein the combination of 1-hydroxy-4-methyl-6-(2,4,4-trimethylpentyl)-2-pyridone monoethanolamine salt and Diethylenetriaminepentakis (methylenephosphonic acid) has a modified fractional inhibitor concentration of 50 ppm
d) from about 40% to about 95% of aqueous carrier.

2. The hair care composition of claim 1 wherein the 1-hydroxy-4-methyl-6-(2,4,4-trimethylpentyl)-2-pyridone monoethanolamine salt material is from about 0.5% to about 2%.

3. The hair care composition of claim 1 wherein the Diethylenetriaminepentakis (methylenephosphonic acid) is from about 0.5% to about 4%.

4. The shampoo composition of claim 1 wherein the hair composition further comprises one or more additional anti-dandruff active agents selected from the group consisting of climbazole, ketoconazole, itraconazole, econazole, elubiol and combinations thereof.

* * * * *